United States Patent
Isenburg et al.

(10) Patent No.: US 12,383,657 B1
(45) Date of Patent: *Aug. 12, 2025

(54) BIOLOGIC MATRIX FOR A WOUND SITE AND RELATED METHODS

(71) Applicant: Reprise Biomedical, Inc., Plymouth, MN (US)

(72) Inventors: Jason Isenburg, Chanhassen, MN (US); Kyle Bettinger, Blaine, MN (US)

(73) Assignee: Reprise Biomedical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/448,250

(22) Filed: Aug. 11, 2023

Related U.S. Application Data

(63) Continuation-in-part of application No. 17/834,561, filed on Jun. 7, 2022, now Pat. No. 12,138,365.

(60) Provisional application No. 63/208,596, filed on Jun. 9, 2021.

(51) Int. Cl.
| | |
|---|---|
| *A61L 27/56* | (2006.01) |
| *A61L 27/24* | (2006.01) |
| *A61L 27/54* | (2006.01) |
| *A61L 27/58* | (2006.01) |

(52) U.S. Cl.
CPC ............ *A61L 27/56* (2013.01); *A61L 27/24* (2013.01); *A61L 27/54* (2013.01); *A61L 27/58* (2013.01); *A61L 2300/404* (2013.01)

(58) Field of Classification Search
None
See application file for complete search history.

(56) References Cited

U.S. PATENT DOCUMENTS

| | | |
|---|---|---|
| 3,545,221 A | 12/1970 | Swenson et al. |
| 3,639,084 A | 2/1972 | Richard |
| 4,801,299 A | 1/1989 | Brendel et al. |
| 6,376,244 B1 | 4/2002 | Atala |
| 6,379,963 B2 | 4/2002 | Haverich et al. |
| 6,416,995 B1 | 7/2002 | Wolfinbarger |
| 6,432,712 B1 | 8/2002 | Wolfinbarger |
| 6,479,064 B1 | 11/2002 | Atala |
| 6,689,161 B2 | 2/2004 | Chen et al. |
| 6,753,181 B2 | 6/2004 | Atala |
| 6,960,427 B2 | 11/2005 | Haverich et al. |
| 6,962,814 B2 | 11/2005 | Mitchell et al. |
| 7,311,904 B2 | 12/2007 | Hariri |
| 7,354,749 B2 | 4/2008 | Fisher et al. |
| 8,470,520 B2 | 6/2013 | Ott et al. |
| 9,974,814 B2 | 5/2018 | Katane et al. |
| 11,602,548 B1 | 3/2023 | Klitzke et al. |
| 11,998,662 B1 | 6/2024 | Isenburg et al. |
| 12,115,284 B1 | 10/2024 | Isenburg et al. |
| 12,138,365 B1 | 11/2024 | Isenburg |
| 2001/0049138 A1 | 12/2001 | Dennis et al. |
| 2002/0081728 A1 | 6/2002 | Haverich et al. |
| 2003/0087428 A1 | 5/2003 | Wolfinbarger et al. |
| 2003/0096407 A1 | 5/2003 | Atala et al. |
| 2003/0124099 A1 | 7/2003 | Atala |
| 2003/0215945 A1 | 11/2003 | Atala |
| 2004/0176855 A1 | 9/2004 | Badylak |
| 2005/0084512 A1 | 4/2005 | Denizeau et al. |
| 2005/0249816 A1 | 11/2005 | Atala et al. |
| 2005/0266390 A1 | 12/2005 | Ueda et al. |
| 2007/0059293 A1 | 3/2007 | Atala |
| 2008/0058956 A1 | 3/2008 | Badylak |
| 2009/0202977 A1 | 8/2009 | Ott et al. |
| 2011/0011410 A1 | 1/2011 | Desai et al. |
| 2012/0183944 A1 | 7/2012 | Taylor et al. |
| 2015/0182560 A1 | 7/2015 | Calle et al. |
| 2016/0030638 A1 | 2/2016 | Ross et al. |
| 2016/0279170 A1* | 9/2016 | Katane ............... A61L 27/3683 |

(Continued)

FOREIGN PATENT DOCUMENTS

| | | |
|---|---|---|
| CN | 101272815 B | 9/2012 |
| CN | 107635592 A | 1/2018 |
| EP | 1246903 A1 | 10/2002 |

(Continued)

OTHER PUBLICATIONS

Silvestry-Rodriguez, N., et al., Rev Environ Contam Toxicol 191: 23-45 (2007). (Year: 2007).*
Uygun, B., et al., Nature Mediciene 16(7): 814 â 821 (Jul. 2010). (Year: 2010).*
Lee, "GraftJacket Augmentation of Chronic Achilles Tendon Ruptures," Orthopedics, 2004, 27:151-153.
Levenberg et al., "Engineering vascularized skeletal muscle tissue," Nat. Biotechnol., 2005, 23(7):879-884.
L'Heureux et al., "Human tissue-engineered blood vessels for adult arterial revascularization," Nat. Med., 2006, 12(3):361-365.
Lichtenberg et al., "Flow-Dependent Re-Endothelialization of Tissue-Engineered Heart Valves," J. Heart Valve Dis., 2006, 15:287-294.
Lin et al., "Assembling Porcine Liver-Derived Biomatrix for Hepatic Tissue Engineering," Tissue Eng., 2004, 10:1046-1053.

(Continued)

*Primary Examiner* — David J Blanchard
*Assistant Examiner* — Daniel F Coughlin
(74) *Attorney, Agent, or Firm* — Gregory W. Smock

(57) ABSTRACT

A biologic matrix comprises a three-dimensional, resorbable collagen scaffold derived from a vascularized portion of a perfusion-decellularized, suspension-dried mammalian organ or tissue. The scaffold features a porous structure with a plurality of interconnected pores originating from one or more of its outer surfaces. The pores are created by forcing a gas through the vascular pathways of the mammalian organ or tissue while it is in a suspended position. This enables the gas to inflate the vascular pathways in all directions without restriction. The porous configuration substantially enhances the scaffold's effective surface area, making it at least 10 times greater than that of a non-porous scaffold having equivalent outer dimensions. In certain embodiments, the surface area considering the interconnected pores can be 15 times larger or more than the non-porous scaffold of equivalent outer dimensions.

17 Claims, 6 Drawing Sheets

(56) References Cited

U.S. PATENT DOCUMENTS

2025/0032671 A1    1/2025    Isenburg

FOREIGN PATENT DOCUMENTS

| | | | |
|---|---|---|---|
| EP | 1928519 B1 | 4/2012 | |
| ES | 2384721 | 7/2012 | |
| RU | 2463081 C2 | 10/2012 | |
| WO | 1996008213 A1 | 3/1996 | |
| WO | WO-9933447 A2 * | 7/1999 | ............. A61L 27/56 |
| WO | 2001048153 A1 | 7/2001 | |
| WO | 2001049210 A1 | 7/2001 | |
| WO | 2002024244 A2 | 3/2002 | |
| WO | 2002040630 A2 | 5/2002 | |
| WO | 2002049681 A1 | 6/2002 | |
| WO | 2002063962 A1 | 8/2002 | |
| WO | 2003039610 A1 | 5/2003 | |
| WO | 2003043674 A1 | 5/2003 | |
| WO | 2003087428 A1 | 10/2003 | |
| WO | 2004080501 A1 | 9/2004 | |
| WO | 2004100832 A1 | 11/2004 | |
| WO | 2005118014 A2 | 12/2005 | |
| WO | 2006033415 A1 | 3/2006 | |
| WO | 2006122533 A2 | 11/2006 | |
| WO | 2007025233 A1 | 3/2007 | |
| WO | 2010120539 A2 | 10/2010 | |
| WO | 2011031484 A2 | 3/2011 | |
| WO | 2011066522 A2 | 6/2011 | |
| WO | 2012031162 A1 | 3/2012 | |
| WO | 2014013241 A1 | 1/2014 | |
| WO | 2014059316 A1 | 4/2014 | |
| WO | 2016154447 A1 | 9/2016 | |

OTHER PUBLICATIONS

Matsuura et al., "Cellular Remodeling of Depopulated Bovine Ureter Used as an Arteriovenous Graft in the Canine Model," J. Am Coll. Surg., 2004, 198(5):778-783.

Matthiesen, Thomas, et al. "Abstract 428: Creating Biocompatible 3-D Scaffolds for Engineering Cardiovascular Tissues: Heart, Lung, and Kidney," Circulation, 2007, vol. 116, No. 16( suppl. S), p. 70 (abstract only).

Matthiesen, Thomas, et al. "Abstract 572: Large Solid Organ Perfusion Decellularization: A Start for Human-Sized Tissue Scaffolds?" Circulation, 2007, vol. 116, No. 16( suppl. S), p. 103 (abstract only).

Mazzetti et al., "Molecular anatomy of the cerebral microvessels in the isolated guinea-pig brain," Brain Res., 2004, 999:81-90.

McFetridge et al., "Preparation of porcine carotid arteries for vascular tissue engineering applications," J. Biomed. Mater. Res. A. 2004, 70A:224-234.

Mirsadraee et al., "Development and Characterization of an Acellular Human Pericardial Matrix for Tissue Engineering," Tissue Eng., 2006, 12(4):763:773.

Miyagawa et al., "Tissue Cardiomyoplasty Using Bioengineered Contractile Cardiomyocyte Sheets to Repair Damaged Myocardium: Their Integration with Recipient Myocardium," Transplantation, 2005, 80(11):1586-1595.

Niklason et al.., "Functional Arteries Grown in Vitro," Science, 1999, 284:489-493.

Oliver et al., "Dermal Collagen Implants," Biomaterials, 1982, 1:38-40.

Ott et al., "Cell-based cardiovascular repair. The Hurdles and the Opportunities," Basic Res. Cardiol., 2005, 100:504-517.

Ott et al., "Perfusion-Decellularized Matrix: Using Nature's Platform to Engineer a Bioartificial Heart," Nat. Med., 2008, 14(2):213-221.

Ott et al., "Regeneration and orthotopic transplantation of a bioartificial lung", Nature Medicine, Advance Online Publication, (2010) 8 pgs.

Park et al., "A novel composite scaffold for cardiac tissue engineering," In Vitro Cell Dev. Biol. Anim., 2005, 41:188-196.

PCT International Application Serial No. PCT/US2016/024032, International Preliminary Report on Patentability dated Oct. 5, 2017, 10 pgs.

PCT International Application Serial No. PCT/US2016/024032, International Search Report dated Aug. 26, 2016, 5 pgs.

PCT International Application Serial No. PCT/US2016/024032, Written Opinion dated Aug. 26, 2016, 8 pgs.

Pelham et al., "Cell locomotion and focal adhesions are regulated by substrate flexibility," Proc. Natl. Acad. Sci. USA, 1997, 94:13661-13665.

Peters, J.M. et al. "Organ Weights and Water Levels of the Rat following Reduced Food Intake," The Journal of Nutrition, 1966, vol. 90: 354-360.

Petersen et al., "Tissue-engineered lungs for in vivo implantation", Science Express, www.sciencexpress.org, (Jun. 24, 2010) 10 pgs.

Phillips et al., "Neural Tissue Engineering: A Self-Organizing Collagen Guidance Conduit," Tissue Eng., 2005, 11:1611-1617.

Powers et al., "Functional Behavior of Primary Rat Liver Cells in a Three-Dimensional Perfused Microarray Bioreactor," Tissue Eng., 2002, 8(3):499-513.

Radisic et al., "Mathematical model of oxygen distribution in engineered cardiac tissue with parallel channel array perfused with culture medium containing oxygen carriers," Am. J. Physiol. Heart Circ. Physiol., 2005, 288:H1278-H1289.

Rieder et al., "Decellularization protocols of porcine heart valves differ importantly in efficiency of cell removal and susceptibility of the matrix to recellularization with human vascular cells," J. Thorac. Cardiovasc. Surg., 2004, 127:399-405.

Robinson et al., "Extracellular Matrix Scaffold for Cardiac Repair," Circulation, 2005, 112[suppl I]: I-135-I-143.

Roy et al., "Biomechanical properties of decellularized porcine common carotid arteries," Am. J. Physiol. Heart Circ. Physiol., 2005, 289:H1567-H1576.

Sayk et al., "Histopathologic Findings in a Novel Decellularized Pulmonary Homograft: An Autopsy Study," Ann. Thorac. Surg., 2005, 79(5):1755-1758.

Schaner, Patrick, J. "Decellularized vein as a potential scaffold for vascular tissue engineering," Journal of Vascular Surgery, Jul. 2004, 40(1): 146-153.

Schenke-Layland, K. et al. "Complete dynamic repopulation of decellularized heart valves by application of defined physical signals: an in vitro study," Cardiovascular Research, 2003, 60: 497-509.

Schlager, Gunther. "Kidney Weight in Mice: Strain Differences and Genetic Determination," The Journal of Heredity, May 1968, 59(3): pp. 171-174.

Schmidt, Christine E., et al. "Acellular vascular tissues: natural biomaterials for tissue repair and tissue engineering," Biomaterials, 2000, 21: 2215-2231.

Sekine et al., "Cardiomyocyte Bridging Between Hearts and Bioengineered Myocardial Tissues with Mesenchymal Transition of Mesothelial Cells," J. Heart Lung Transplant., 2006, 25:324-332.

Shimizu, Tatsuya, et al. "Fabrication of Pulsatile Cardiac Tissue Grafts Using a Novel 3-Dimensional Cell Sheet Manipulation Technique and Temperature-Responsive Cell Culture Surfaces," Circulation Research, Feb. 22, 2002, 90: e40-e48.

Shyy et al., "Role of Integrins in Endothelial Mechanosensing of Shear Stress," Circ. Res., 2002, 91:769-775.

Stevenson et al., "Left Ventricular Assist Device as Destination for Patients Undergoing Intravenous Inotropic Therapy. A Subset Analysis from REMATCH (Randomized Evaluation of Mechanical Assistance in Treatment of Chronic Heart Failure)," Circulation, 2004, 110:975-981.

Sudo et al., "Reconstruction of 3D stacked-up structures by rat small hepatocytes on microporous membranes," Faseb J., 2005, 19:1695-1697.

Sun et al., "Development of a Closed Bioreactor System for Culture of Tissue-Engineered Skin at an Air-Liquid Interface," Tissue Eng., 2005, 11:1824-1831.

Takagi, Kazuyoshi, et al. "In Vivo Recellularization of Plain Decellularized Xenografts With Specific Cell Characterization in the Systemic Circulation: Histological and Immunohistochemical Study," Artificial Organs, 2006, 30(4): 233-241.

(56) References Cited

OTHER PUBLICATIONS

Taylor et al., "Regenerating functional myocardium: Improved performance after skeletal myoblast transplantation," Nat. Med., 1998, 4(8):929-933.
Teebken et al. "Tissue-Engineering: In Vitro Creation of Tissue Substitutes," Zentralbl Chir, 2007, 132: 236-246.
Teebken et al., "Tissue engineering of vascular grafts: human cell seeding of decellularised porcine matrix," Eur. J. Vasc. Endovasc. Surg., 2000, 19:381-386.
Toni, Roberto, et al. "The bioartificial thyroid: a biotechnological perspective in endocrine organ engineering for transplantation replacement," Act Biomed, 2007, 78 (suppl 1): 129-155.
Uchimura et al., "Novel method of preparing acellular cardiovascular grafts by decellularization with poly(ethylene glycol)," J. Biomed. Mater. Res., 2003, 67A:834-837.
Uygun et al., "Organ reengineering through development of a transplantable recellularized liver graft using decellularized liver matrix.", Nature Medicine, Advance Online Publication, (2010) 8 pgs.
Wagner et al., "The isolated normothermic hemoperfused porcine forelimb as a test system for transdermal absorption studies," J. Artif. Organs, 2003, 6(3):183-191.
Walles, T. et al. "Acellular scaffold implantation—no alternative to tissue engineering," The International Journal of Artificial Organs. 2003, 26(3):225-234.
Wang et al., "Reconstruction of Renal Glomerular Tissue Using Collagen Vitrigel Scaffold," J. Biosci. Bioeng., 2005, 99(6):529-540.
Woods et al., "Effectiveness of three extraction techniques in the development of a decellularized bone-anterior cruciate ligament-bone graft," Biomaterials, 2005, 26:7339-7349.
Zandonella, Catherine. "The beat goes on," Nature, Feb. 2003, 412: 884-886.
Zeltinger, Joan, et al. "Development and Characterization of Tissue-Engineered Aortic Valves," Tissue Engineering, 2001, 7(1): 9-22.
Zimmerman et al., "Engineered heart tissue grafts improve systolic and diastolic function in infarcted rat hearts," Nat. Med., 2006, 12(4):452-458.
Zimmerman, Wolfram-Hubertus, et al. "Engineered Heart Tissue for Regeneration of Diseased Hearts," Biomaterials, 2004, 25:1639-1647.
Atala et al., "Tissue-engineered autologous bladders for patients needing cystoplasty," Lancet, 2006, 367:1241-1246.
Atala, "Recent developments in tissue engineering and regenerative medicine," Curr. Opin. Pediatr., 2006, 18:167-171.
Bader et al., "Tissue engineering of heart valves-human endothelial cell seeding of detergent acellularized porcine valves," Eur. J. Cardiothorac. Surg., 1998, 14:279-284.
Badylak, "Xenogeneic extracellular matrix as a scaffold for tissue reconstruction," Transpl. Immunol., 2004, 12:367-377.
Baertschiger et al, "Xenotransplantation Literature Update Nov.-Dec. 2005," Xenotransplantation, 2006, 13:96-99.
Baptista, Pedro, et al. "A Novel Acellular and Biologically Derived Scaffold for Tissue Engineering," [online]. Pittsburgh Tissue Engineering Initiative, 2005, [retrieved on Jul. 27, 2005]. Retrieved from the Internet.
Baptista, Pedro, et al. "A Novel Whole Organ Bioscaffold for Tissue Engineering and Regenerative Medicine Applications," The FASEB Journal, 2007, 21:902.6, abstract only.
Baptista, Pedro, et al. "The Use of Whole Organ Decellularization for the Generation of a Vascularized Liver Organoid," Hepatology, Feb. 2011, 53(2): 604-617.
Bodnar et al., "Damage of Porcine Aortic Valve Tissue Caused by the Surfactant Sodiumdodecylsulphate," Thorac. cardiovasc. Surg., 1986, 34:82-85.
Borschel et al., "Contractile Skeletal Muscle Tissue-Engineered on an Acellular Scaffold," Plast. Reconstr. Surg., 2004, 113:595-602.
Brendel, Klaus, et al. "The Accelular Perfused Kidney: A Model for Basement Membrane Permeability," Biology and Chemistry of Basement Membranes, 1978, pp. 177-193.
Cartmell et al., "Development of Cell-Seeded Patellar Tendon Allografts for Anterior Cruciate Ligament Reconstruction," Tissue Eng., 2004, 10:1065-1075.
Cebotari, Serghei, et al. "Construction of Autologous Human Heart Valves Based on an Accelular Allograft Matrix," Circulation, Sep. 24, 2002, pp. 63-68.
Chen et al., "Acellular collagen matrix as a possible "off the shelf" biomaterial for urethral repair," Urology, 1999, 54:407-410.
Chen et al., "Experimental and clinical experience using tissue regeneration for urethral reconstruction," World J. Urol., 2000, 18:67-70.
Chen et al., "Process development of an acellular dermal matrix (ADM) for biomedical applications," Biomaterials, 2004, 25:2679-2686.
Conconi et al., Homologous muscle acellular matrix seeded with autologous myoblasts as tissue-engineering approach to abdominal wall-defect repair, Biomaterials, 2005, 26:2567-2574.
Courtman et al., "Development of a pericardial acellular matrix biomaterial: Biochemical and mechanical effects of cell extraction," J. Biomed. Mater. Res., 1994, 28:655-666.
Crapo, Peter, et al. "An overview of tissue and whole organ decellularization processes," Biomaterials, 2011, 32:3233-3243.
Dahl et al., "Decellularized Native and Engineered Arterial Scaffolds for Transplantation," Cell Transplant., 2003, 12:659-666.
Davis et al., "Endothelial Extracellular Matrix: Biosynthesis, Remodeling, and Functions During Vascular Morphogenesis and Neovessel Stabilization," Circ. Res., 2005, 97:1093-1107.
Dellgren et al., "Eleven years' experience with the Biocor stentless aortic bioprothesis: clinical and hermodynamic follow-up with long-term relative survival rate," Eur. J. Cardiothorac. Surg., 2002, 22:912-921.
Den Butter et al., "Comparison of solutions for preservation of the rabbit liver as tested by isolated perfusion," Transpl. Int., 1995, 8:466-471.
Deng et al., "Destination Mechanical Circulatory Support: Proposal for Clinical Standards," J. Heart Lung Transplant, 2003, 22:365-369.
Deyl et al. "Steric Hindrances in Protein Permeation Through the Basement Membrane Studied in Acellular Kidney," Physiologia Bohemoslovaca 36(5):425-434, 1987.
Elkins et al., "Decellularized Human Valve Allografts," Ann. Thorac. Surg., 2001, 71(suppl 5):S428-432.
Engbers-Buijtenhuijs, Paula, et al, "Biological characterisation of vascular grafts cultured in a bioreactor," Biomaterials, 2006, 27:2390-2397.
Eschenhagen, Thomas, et al., "Engineering Myocardial Tissue," Circ. Res., 2005, 97:1220-1231.
Firth et al., "Sodium handling in the isolated perfused kidney of the cirrhotic rat," Clin. Sci., 1989, 77(6):657-661.
Furuta et al., "Pulsatile Cardiac Tissue Grafts Using a Novel Three-Dimensional Cell Sheet Manipulation Technique Functionally Integrates with the Host Heart, In Vivo," Circ. Res., 2006, 98:705-712.
Gerecht-Nir, Sharon, et al., "Biophysical regulation during cardiac development and application to tissue engineering," Int. J. Dev. Biol., 2006, 50:233-243.
Gilbert et al., "Decellularization of tissues and organs," Biomaterials, 2006, 27:3675-3683.
Grabow et al., "Mechanical and Structural Properties of a Novel Hybrid Heart Valve Scaffold for Tissue Engineering," Artif. Organs, 2004, 28(11):971-979.
Groetzner et al., "Results of Pediatric Cardiac Transplantation-Long-Term Results of a 15-Year Experience," Thorac. Cardiov. Surg., 2005, 53(Suppl 2):S149-S154.
Hohfield et al., "Tissue engineered fetal skin constructs for paediatric burns," Lancet, 2005, 366:840-842.
Hopper et al. "Acellularization of Human Placenta with Preservation of the Basement Membrane," Ann Plast Surg 51(6):598-602, Dec. 2003.
Hou et al., "Tissue-engineered peripheral nerve grafting by differentiated bone marrow stromal cells," Neuroscience, 2006, 140:101-110.

(56) References Cited

OTHER PUBLICATIONS

Hudson et al., "Engineering an Improved Acellular Nerve Graft via Optimized Chemical Processing," Tissue Eng., 2004, 10:1346-1358.
Ikeda et al., "Growing bioengineered teeth from single cells: potential for dental regenerative medicine," Expert Opin. Biol. Ther., 2008, 8(6):735-744.
Isenberg et al., "Small Diameter Artificial Arteries Engineered In Vitro," Circ. Res., 2006, 98:25-35.
Jawad et al., "Myocardial Tissue Engineering," British Medical Bulletin, 2008, 87:31-47.
Juncosa-Melvin, Natalia, et al., "The Effect of Autologous Mesenchymal Stem Cells on the Biomechanics and Histology of Gel-Collagen Sponge Constructs Used for Rabbit Patellar Tendon Repair," Tissue Eng., 2006, 12:369-379.
Kasimir, Marie-Theres, et al. "The decellularied porcine heart valve matrix in tissue engineering: Platelet adhesion and activation," Throm. Haemost., 2005, 94:562-567.
Ketchedjian et al., "Recellularization of Decellularized Allograft Scaffolds in Ovine Great Vessel Reconstructions," Ann. Thorac. Surg., 2005, 79:888-896.
Knight et al., "Tissue Engineering of Cardiac Valves: Re-Seeding of Acellular Porcine Aortic Valve Matrices with Human Mesenchymal Progenitor Cells," J. Heart Valve Dis., 2005, 14:806-813.
Kofidis et al., "Myocardial Restoration and Tissue Engineering of Heart Structures," Methods Mol. Med., 2007, 140:273-290.
Kolker et al., "Multilayer Reconstruction of Abdominal Wall Defects with Acellular Dermal Allograft (AlloDerm) and Component Separation," Ann. Plast. Surg., 2005, 55:36-41.
Kren, Stefan, et al. "Abstract 580: The Production of a Bio-Engineered Endothelial Intima From Cultured Cells Using Whole Cardiac Cadaveric Extracellular Matrix," Circulation, 2007, 116:(16): 105 (abstract only).
Ladhoff, Juliane, et al., "Immune privilege of endothelial cells differentiated from endothelial progenitor cells", Cardiovascular Research, 2010, 88:121-129.
Langer et al, "Tissue Engineering," Science, 1993, 260:920-926.
U.S. Appl. No. 18/448,259, filed Aug. 11, 2023, Biologic Matrix for a Wound Site and Related Methods.
"U.S. Appl. No. 18/448,259, Examination Report mailed Feb. 29, 2024," 26 pgs.
Mostow, E., et al. "Effectiveness of an extracellular matrix graft (Oasis Wound Matrix) in the treatment of chronic leg ulcers; A randomized clinical trial," J Vasc Surg 41: 837-843 (2005).
"U.S. Appl. No. 18/448,259, response to first Examination Report, filed Mar. 6, 2024" 8 pgs.
"U.S. Appl. No. 17/834,561, Examination Report mailed Nov. 28, 2023," 11 pgs.
Mattei, Giorgio et al. "Decellularised Human Liver is too Heterogeneous for Designing a Generic ECM-mimic Hepatic Scaffold," Artificial Organs 41(12): E347-E355 (2017).
"U.S. Appl. No. 17/834,561, Response to Examination Report, filed Feb. 27, 2024," 11 pgs.
"U.S. Appl. No. 18/624,746, Office Action mailed May 31, 2024," 27 pgs.
"U.S. Appl. No. 17/834,561, Response to 2nd Examination Report, filed Aug. 16, 2024," 19 pgs.
"U.S. Appl. No. 18/624,746, Response to 1st Office Action, filed Aug. 12, 2024," 9 pgs.
"U.S. Appl. No. 17/834,561, Examination Report mailed Apr. 16, 2024," 18 pgs.
"U.S. Appl. No. 18/908,461, Office Action mailed Dec. 9, 2024," 26 pgs.
An, Yoojin, et al. "Computed tomographic measurements of pancreatic thickness in clinically normal dogs," Frontiers in Veterinary Science, vol. 10, (2023), pp. 1-11. (Year: 2023).
Seppelt, D. et al. "Simple diameter measurement as predictor of liver volume and liver parenchymal disease," Scientific Reports, vol. 12, Article No. 1257 (2022), pp. 1-8. (Year: 2022).
"U.S. Appl. No. 18/908,461, Non-Final Office Action mailed Apr. 17, 2025," 26 pgs.
"U.S. Appl. No. 18/908,461, Response to Office Action filed Mar. 7, 2025," 16 pgs.
Heinz et al. "Manual on Simple Methods of Meat Preservation," Agricultural and Food Sciences, 1990, pp. 1-27.

\* cited by examiner

5cm x 10cm x 2cm

5cm x 5cm x 2cm

3cm x 3cm x 2cm

2cm x 2cm x 2cm

BIOLOGIC MATRIX FOR A WOUND SITE AND RELATED METHODS

CLAIM OF PRIORITY

This continuation-in-part application claims the benefit of priority under 35 U.S.C. § 120 to U.S. patent application Ser. No. 17/834,561, titled "DRY INFLATED DECELLULARIZED EXTRACELLULAR MATRIX," filed on Jun. 7, 2022, and to U.S. provisional patent application Ser. No. 63/208,596, titled "DRY INFLATED DECELLULARIZED EXTRACELLULAR MATRIX," filed on Jun. 9, 2021. These earlier-filed applications are incorporated herein by reference in their entirety.

FIELD OF INVENTION

The present subject matter relates to biologic matrices designed for wound care and tissue regeneration, and further relates to augmenting a void or treating a wound in a body cavity of a mammal.

BACKGROUND

Wound healing and tissue regeneration are essential processes in the field of medicine, requiring advanced biomaterials that facilitate cellular infiltration, integration, and remodeling. Biologic matrices derived from perfusion-decellularized mammalian organs or tissues hold promise in promoting wound healing and tissue regeneration due to their preserved extracellular matrix components. The extracellular matrix can play a vital role in cell attachment, migration, and tissue repair processes.

OVERVIEW

The present inventors recognized a need for biologic matrices with enhanced effective surface area and porosity to facilitate wound healing and tissue regeneration. They developed three-dimensional, resorbable collagen scaffolds derived from perfusion-decellularized mammalian organs or tissues. The scaffolds possess a porous structure with interconnected pores emanating from one or more outer surfaces, significantly increasing the effective surface area compared to non-porous scaffolds of the same or similar outer dimensions. This enhanced surface area promotes cellular infiltration, integration, and remodeling, contributing to accelerated wound healing and improved patient outcomes.

In one aspect, the biologic matrix includes a plurality of interstitial voids within the porous structure, allowing for cellular infiltration within two weeks post-implant, integration of native collagen within three weeks post-implant, and full remodeling by twelve weeks post-implant.

In another aspect, the biologic matrix incorporates antimicrobial agents, such as silver or methylene blue, which are perfused into the vascular pathways of the mammalian organ or tissue following its perfusion decellularization. This feature enhances the matrix's antimicrobial properties and aids in preventing infection at the wound site.

Furthermore, the biologic matrix can be designed to be transparent or translucent, enabling non-invasive visual monitoring of the wound site without the need for removal. This transparency or translucency allows medical practitioners to assess the healing progress in real-time, facilitating precise treatment adjustments.

The biologic matrix's mechanical strength is sufficient to be sutured or stapled to body tissue surrounding the wound site, ensuring stable integration and support during the healing process.

The present subject matter also encompasses methods for manufacturing the collagen matrix, involving the steps of obtaining a mammalian organ or vascularized portion thereof or a vascularized mammalian tissue, decellularizing the organ or tissue via perfusion decellularization through vascular pathways, and inflating the decellularized organ or tissue with a gas. The gas is introduced through the vascular pathways, causing the organ or tissue to expand three-dimensionally relative to its non-inflated configuration.

The present subject matter further provides a method for augmenting a void or treating a wound in a body cavity of a mammal, wherein a three-dimensional, resorbable collagen scaffold derived from a vascularized portion of a perfusion-decellularized mammalian organ or tissue is applied to the site of the void or body cavity. The scaffold is applied by contacting at least three of its surfaces with body tissue surrounding the void or body cavity. The method enables cellular infiltration, integration, or remodeling of the surrounding body tissue into one or more vascular pathways of the scaffold, promoting effective wound healing and tissue regeneration.

These and other examples and features of the present biologic matrices and related methods will be set forth, at least in part, in the following Detailed Description. This Overview is intended to provide non-limiting examples of the present subject matter—it is not intended to provide an exclusive or exhaustive explanation. The Detailed Description below is included to provide further information about the present biologic matrices and related methods.

BRIEF DESCRIPTION OF THE FIGURES

The drawings illustrate generally, by way of example, but not by way of limitation, various biologic matrices and related methods discussed in this patent document.

Figure 1:
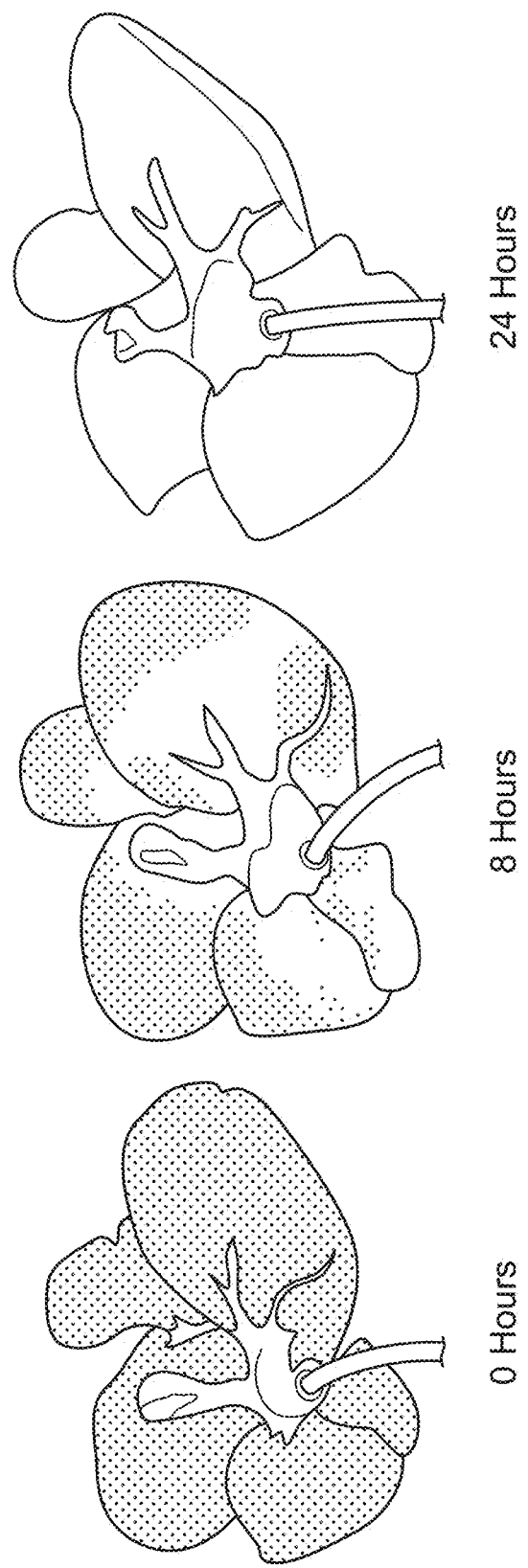
FIG. 1 illustrates sequential images of a liver during a decellularization process, as constructed in accordance with at least one embodiment.

The drawings are not necessarily to scale. Certain features and components may be exaggerated in scale or in schematic form, and some details may not be shown in the interest of clarity and conciseness.

DETAILED DESCRIPTION

The present subject matter pertains to a process for decellularizing organs or tissues to obtain an acellular organ or tissue containing an extracellular matrix. A decellularized solution, or a suitable alternative, is introduced into the organ or tissue to replace the space previously occupied by cells. However, in certain organs and tissues, like the liver, lung, muscle, spleen, and heart, removing cells can cause compartments to collapse and the original shape to shrink.

To preserve the three-dimensional structure and original shape, a gas or gas with particles or droplets (vapor) can be introduced into at least one vessel, duct, or cavity. This introduction fills the void spaces, creating a three-dimensional matrix that retains its shape and prevents compartment collapse. The resulting three-dimensional matrix can be cut, shaped, and molded for various applications without compromising its structural integrity, offering significant potential for practical uses.

Sources of Organs and Tissues for Decellularized ECM:

Tissues are groups of cells that share a common structure and function. There are different types, like epithelial tissue, connective tissue, muscle tissue (skeletal, cardiac, or smooth muscle), and nervous tissue. Tissues form flexible sheets that cover, line, or connect organs.

In contrast, an organ consists of two or more tissues joined together to serve a specific function. Organs include the brain, liver, pancreas, bone, spleen, heart, stomach, kidney, lungs, whole muscles, thymus, anus, and intestine, among others. Organs can be whole organs, parts of an organ, or vascularized structures.

In the methods described here, a portion of an organ or tissue or its extracellular matrix (ECM) can be used. For example, a portion of the heart (atrium or ventricle) or the interior structure of the pancreas (including islets) may be employed. These portions can be about 5 to 10 millimeters (mm) or about 70 to 100 mm thick.

The ECM of an organ or tissue, or a vascularized portion, can be obtained from various sources, such as the heart, liver, lungs, skeletal muscles, brain, pancreas, spleen, kidneys, uterus, eye, spinal cord, intestine, omentum, whole muscles, bladder, and more. A solid organ is one with a "substantially closed" vasculature system, meaning that when perfused with liquid, the majority of the liquid stays within the organ or flows through its native vascular structures without leaking out, assuming the major vessels are properly managed. Certain organs may have "entrance" and "exit" vessels, which are used to introduce and move the perfusion liquid throughout the organ.

Perfusion decellularized matrices of organs with a substantially closed vascular system are valuable because they preserve the intact matrix and microenvironment, including the vascular and microvascular system. These preserved structures can be used to deliver nutrients and growth factors to the organ. Nutrients and growth factors may be delivered by various means, such as injection or passive diffusion, alone or in combination.

Perfusion Decellularization:

In certain embodiments, this disclosure includes methods that involve perfusion-based decellularization of a solid organ or a portion of it. Perfusion decellularization allows for rapid removal of cells through the organ's native vasculature, ducts, cavities, or a combination, while preserving critical vascular conduits necessary for tissue re-engineering.

Using perfusion decellularization, access to a whole organ can be attained by cannulating a blood vessel and passing a mild detergent solution through it. Organs have a dense network of vascular capillaries, with most cells located within 50-100 micrometers (μm) of a capillary. This leads to a much larger effective surface area for the detergent, resulting in faster dissolution of cellular material as it is expelled through the venous system compared to immersion-based decellularization, where it is expelled through an isolated organ wall or capsule.

One significant advantage of perfusion decellularization is its ability to retain the native microstructure of the extracellular matrix (ECM) from an isolated organ or tissue, including an intact vascular and/or microvascular system. This preservation is not always possible with other decellularization techniques, such as immersion-based methods. For instance, perfusion decellularized ECM from organs or tissues can maintain collagen content, binding and signaling factors, and vasculature structure, providing a niche environment with native cues for functional differentiation or maintaining cellular function of introduced cells.

To replicate conditions found in an organism, perfusion decellularized ECM from organs or tissues can be perfused with cells and/or media using appropriate pressure and flow through the vasculature. The normal pressure of human-sized organs can range between about 5 mm Hg to about 200 mm Hg, depending on the diameter of the incoming perfusion vessel.

The perfusion decellularization process involves a cannulation system, where one or more cannulas are introduced to an isolated organ or portion thereof, with the number of cannulations varying depending on the specific application. Different gauge cannulas may be used, with sizes ranging from 1 to 75, depending on the organ or tissue being processed.

During organ perfusion, various solutions and media can be used, including cellular disruption media, washing solutions, and disinfecting solutions. The cellular disruption media may contain detergents like Sodium dodecyl sulfate (SDS), Polyethylene glycol p-(1,1,3,3-tetramethylbutyl)-phenyl ether (Triton X), NP-40, Brij, Polyoxyethylene sorbitan monolaurate (Tween), Octyl glucoside, octyl thioglucoside, 3-[(3-cholamidopropyl)dimethylammonio]-1-propanesulfonate (CHAPS), 3-[(3-Cholamidopropyl)dimethylammonio]-2-hydroxy-1-propanesulfonate (CHAPSO), or modified versions thereof.

To maintain stable conditions during perfusion, a chamber, reservoir, or tubing can be water-jacketed, and various sensors can be used to monitor the system and/or the isolated organ or tissue. In some embodiments, a computer-readable storage medium in combination with a programmable processor can be used to control and monitor the decellularization process.

The effectiveness of perfusion decellularization can be evaluated through various means, including histological examination, immunohistochemical staining, and DNA quantification.

Efforts can be made to reduce particulate formation during decellularization by using saline solutions and controlling the eating habits of the mammal.

In conclusion, perfusion-based decellularization offers promising advantages over other methods, preserving native structures. By carefully controlling the process and monitoring various parameters, successful decellularization of organs and tissues can be achieved.

Decellularization of Organs or Tissues:

The decellularization process involves several steps to prepare an organ or tissue, including stabilization, decellularization, renaturing, neutralizing, washing, degrading remaining DNA, disinfecting, and maintaining balance.

The initial step is to cannulate the organ or tissue using appropriate methods and materials, inserting one or more hollow tubes into its vessels, ducts, and/or cavities. Subsequently, a cellular disruption medium is perfused through the cannulated organ or tissue. This perfusion decellularization helps maintain the organ's structure and vasculature, creating pathways for post-implant cellular infiltration, integration, and remodeling. As an example, FIG. 1 shows sequential images of a liver during a decellularization process over a 24-hour period.

On the other hand, immersion technology submerges the organ or tissue in chemicals, potentially causing damage to the capsule, collagen breakdown, scaffold disintegration, and is limited to two-dimensional matrices.

Different cellular disruption media containing detergents, water (to make the medium osmotically incompatible with cells), and enzymes (such as collagenases, dispases, DNases, or proteases) can be employed to decellularize an organ or tissue. The process may include subsequent perfusion with wash solutions and enzymes.

Perfusion in both antegrade and retrograde directions can help decellularize the entire organ or tissue while preserving the ECM. The time and temperature of perfusion depend on the size and weight of the organ or tissue and the specific detergent concentration, generally taking several hours.

A successfully decellularized organ or tissue retains ECM components such as fibronectin, fibrillin, laminin, elastin, various collagens, growth factors, glycosaminoglycans, reticular fibers, and thrombospondin. Successful decellularization means the absence of detectable myofilaments, endothelial cells, smooth muscle cells, and nuclei. The morphology and architecture of the ECM should be well-preserved, and the basal lamina should remain intact.

After decellularization, the ECM's morphology and architecture can be visually and histologically examined to ensure successful decellularization. The ECM fibrils should resemble or be similar to those in an organ or tissue that has not been decellularized.

Example Perfusion Decellularization of Heart:
1. PEG Decellularization Protocol:
    Wash the hearts in 200 ml of PBS containing penicillin, streptomycin, amphotericin B, heparin, and Adenocard (no recirculation).
    Decellularize with 35 ml of polyethylene glycol (PEG; 1 g/mL) for up to 30 minutes (manual recirculation).
    Wash with 500 ml of PBS for up to 24 hours (pump recirculation).
    Repeat the washing step at least twice for 24 hours each time.
    Expose the hearts to 35 ml of DNase I (70 U/mL) for at least 1 hour (manual recirculation).
    Wash again with 500 ml of PBS for at least 24 hours.
2. Triton X and Trypsin Decellularization Protocol:
    Wash the hearts in 200 ml of PBS containing penicillin, streptomycin, amphotericin B, heparin, and Adenocard for at least 20 minutes (no recirculation).
    Decellularize with 0.05% Trypsin for 30 minutes, then perfuse with 500 ml of PBS containing 5% Triton-X and 0.1% ammonium-hydroxide for about 6 hours.
    Perfuse with deionized water for 1 hour, then with PBS for 12 hours.
    Wash the hearts 3 times for 24 hours each time using pump recirculation.
    Perfuse with 35 ml of DNase I (70 U/mL) for 1 hour (manual recirculation).
    Wash twice with 500 ml of PBS for at least 24 hours each time using pump recirculation.
3. 1% SDS Decellularization Protocol:
    Wash the hearts in 200 ml of PBS containing penicillin, streptomycin, amphotericin B, heparin, and Adenocard for at least 20 minutes (no recirculation).
    Decellularize with 500 ml of water containing 1% SDS for about 6 hours using pump recirculation.
    Wash with deionized water for 1 hour, then with PBS for 12 hours.
    Wash the hearts three times with 500 ml of PBS for at least 24 hours each time using pump recirculation.
    Perfuse with 35 ml of DNase I (70 U/mL) for 1 hour (manual recirculation).
    Wash three times with 500 ml of PBS for at least 24 hours each time using pump recirculation.
4. Triton X Decellularization Protocol:
    Wash the hearts with 200 ml of PBS containing penicillin, streptomycin, amphotericin B, heparin, and Adenocard for at least 20 minutes (no recirculation).
    Decellularize with 500 ml of water containing 5% Triton X and 0.1% ammonium hydroxide for at least 6 hours using pump recirculation.
    Perfuse with deionized water for about 1 hour, then with PBS for about 12 hours.
    Wash by perfusing with 500 ml of PBS three times for at least 24 hours each time using pump recirculation.
    Perfuse with 35 ml of DNase I (70 U/mL) for about 1 hour (manual recirculation).
    Wash three times with 500 ml of PBS for about 24 hours each time.

Hearts can be perfused at a coronary perfusion pressure of 60 centimeters (cm) $H_2O$. Optionally, hearts may be submerged in a decellularization chamber and perfused with PBS containing antibiotics for 72 hours (continuous flow of 5 milliliter (mL)/minute) to wash out cellular components and detergent.

Detection of Decellularization:

Successful decellularization can be determined by examining histologic sections for the absence of nucleic acid. Preservation of vascular structures can be assessed by perfusing tissue sections with 2% Evans Blue before embedding. A highly efficient decellularization process can be achieved by first perfusing the organ with a 1% solution of ionic detergent (sodium-dodecyl-sulfate or SDS) dissolved in deionized $H_2O$, at a constant coronary perfusion pressure. Then, the organ should be perfused with a 1% solution of non-ionic detergent (Triton X-100) to remove the SDS and potentially renature the ECM proteins. To ensure clear capillaries and small vessels, intermittent retrograde perfusion with phosphate-buffered solution may be used.

To demonstrate intact vascular structures after decellularization, the decellularized organ can be stained using Langendorff perfusion with Evans Blue. This staining method helps visualize the vascular basement membrane and allows quantification of macro- and micro-vascular density.

Before or after decellularization, and before drying, a physiological buffer is commonly used at physiological pH. Examples of such physiological buffers include phosphate buffer saline (PBS), culture media solutions like DMEM/F12, and buffers with nutritional supplements such as glucose. For instance, a Modified Krebs-Henseleit buffer can be prepared with the following composition (in mM): 118 NaCl, 4.7 KCl, 1.2 $MgSO_4$, 1.2 $KH_2PO_4$, 25 $NaHCO_3$, 11 glucose, 1.75 $CaCl_2$, and 2.0 pyruvate, along with 5 U/L insulin.

Another option is a Krebs buffer containing (in mM): 118 NaCl, 4.7 KCl, 25 $NaHCO_3$, 1.2 $MgSO_4$, 1.2 $KH_2PO_4$, 2 $CaCl_2$, gassed with 95% $O_2$ and 5% $CO_2$, and supplemented with glucose (e.g., 11 mM) or glucose combined with 1- or 1.2-mM palmitate. Additionally, KPS-1 Kidney Perfusion Solution or Krebs-Henseleit buffer containing 118 mM NaCl, 4.7 mM KCl, 1.2 mM MgSO4, 1.2 mM KH2PO4, 26 mM $NaHCO_3$, 8 mM glucose, and 1.25 mM CaCl2, supplemented with 2% BSA, KODMEM medium (Knockout Dulbecco's Modified Eagle's Medium), DMEM, Ham's F12 medium, FBS (fetal bovine serum), FGF2 (fibroblast growth factor 2), KSR, or hLIF (human leukemia inhibitory factor) can be used as physiological buffers.

Controlled System for Decellularizing an Organ or Tissue:

A system for decellularizing an organ or tissue typically consists of several components: at least one cannulation device for inserting tubes into the organ or tissue, a perfusion apparatus to infuse the organ or tissue with fluids through the tubes, and optionally a containment system to maintain a sterile environment.

The cannulation device is designed with appropriate hollow tubing that can be introduced into the blood vessels, ducts, or cavities of the organ or tissue. Usually, multiple vessels or cavities are cannulated in an organ. The perfusion apparatus includes a container for holding the liquid, such as a cellular disruption medium, and a mechanism like a pump, air pressure, or gravity to move the liquid through the organ via the tubes. To ensure sterility during decellularization, various techniques are used, like controlling and filtering the airflow, and perfusing the organ with antibiotics, anti-fungals, or other anti-microbials to prevent the growth of unwanted microorganisms.

The decellularization system can also monitor specific perfusion characteristics such as pressure, volume, flow pattern, temperature, gases, pH, mechanical forces like ventricular wall motion and stress, and electrical stimulation like pacing. Using a pressure-regulated perfusion apparatus is beneficial to avoid large fluctuations in the coronary vascular bed as it changes during decellularization. The effectiveness of perfusion can be evaluated by examining the liquid coming out of the system and tissue sections. Standard methods are used to monitor perfusion volume, flow pattern, temperature, partial $O_2$ and $CO_2$ pressures, and pH.

Sensors can be employed to monitor both the system (bioreactor) and the organ or tissue being decellularized. These sensors can provide information about various parameters, such as the pressure of the liquid moving through the organ, the temperature inside the system and/or the tissue, the pH level, and the rate of flow of the liquid through the tubes. The system also includes means to maintain or adjust these features, such as thermometers, thermostats, electrodes, pressure sensors, overflow valves, valves to control the flow rate, and valves to connect or disconnect fluids for changing the pH. Water-jacketed chambers, reservoirs, and tubing are used to ensure stable conditions, particularly regarding temperature.

The system can be controlled by a computer-readable storage medium and a programmable processor. This storage medium contains instructions that the processor follows, enabling it to receive and process information from sensors and transmit information and instructions back to the bioreactor and/or the organ or tissue. For instance, the system can calculate exposure times and perfusion pressures based on the weight of the organ or tissue entered into the storage medium. It can also record preload and afterload (the pressure before and after perfusion) as well as the flow rate, and adjust perfusion pressure, direction, and type of perfusion solution using pumps and valve controls.

Suspended Inflation:

Active access to the vascular network of a decellularized organ or tissue can be achieved by cannulating, directly injecting into the ECM, or using a positive displacement device. Optionally, the main vein or artery belonging to the decellularized organ or tissue can be sealed. In some cases, other vascular channels may be blocked off to create a closed vascular system.

In one embodiment, a pump, syringe, pressurized gas, canned gas, or a canister containing a gas or vapor optionally comprising proteins, small molecules, drugs, or other agents is used to actively introduce a gas or vapor to a suspended, decellularized organ or tissue. A pump outside the organ or tissue can be applied to distribute introduced gases and/or vapors at specific pump rates and pressures. Pump rates can range from about 10 to about 10,000 mL/min, and pressures from about 1 to about 200 mmHg.

Figure 2:
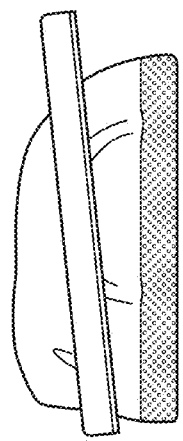
FIG. 2 illustrates a pump used to actively introduce gas to a suspended, decellularized liver through tubing connected to a cannulated vessel of the liver, as constructed in accordance with at least one embodiment.
Figure 2:
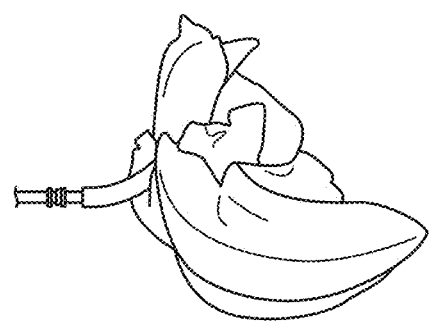
Figure 2:
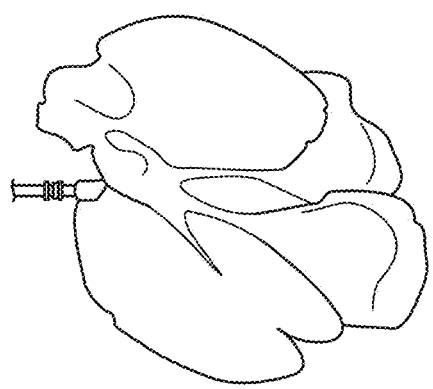

In another embodiment, as shown in FIG. 2, a gas or vapor can be introduced into the decellularized organ or tissue through tubing, cannulas, connectors, needles, and/or syringes connected to a cannulated arterial or venous vessel. The gas or vapor is pumped at a determined rate until desired results are achieved, such as filling to a defined volume, volumetric shape, increased surface tension, and/or increased back pressure.

The resulting gas or vapor-filled and dried decellularized organ or tissue matrix after being cut to a desired size can be used in various therapeutic applications, including surgical fillers, surgical mesh, fillers for fistulas and other voids, and wound beds or cavities. The matrix can also be prepared in granular or morselized pieces, with morsels being about 0.5 mm to about 10 mm in diameter, and granules being smaller, less than about 0.5 mm in diameter.

In some embodiments, the gas-inflated decellularized matrix is used as a shape-retaining surgical filler or for treating fistulas. It can also be subjected to e-beam sterilization or be used to sterilize the decellularized matrix. The inflation of the matrix with a vapor can induce remodeling in vivo and increase cellular engraftment when seeded with cells, or it can be used to slowly release drugs in vivo as a controlled delivery vehicle or carrier.

The disclosure provides an inflated and suspension-dried decellularized extracellular matrix of a mammalian organ or tissue, with a decellularized vascular tree, duct, or cavity, retaining the morphology of the original extracellular matrix prior to decellularization. The matrix can be employed for various applications, and portions of the matrix can be used in different sizes and shapes.

Additionally, methods of inflating and suspension drying a decellularized extracellular matrix, preparing gas-filled (inflated), dried decellularized extracellular matrix, and using the matrix to augment a void or treat wounds are provided. The gas can be air, nitrogen, oxygen, or a vapor with various drugs or proteins. The resulting product can be compressed, sterilized, and applied dry or wetted before application to a wound.

Biologic Matrices for Wound Sites:

The biologic matrices described in this patent application consist of a resorbable collagen scaffold obtained through a perfusion-decellularization process, which removes cellular components while preserving the extracellular matrix of the organ or tissue, such as the liver. By introducing numerous interconnected pores within the scaffold, the effective surface area of the matrix is significantly increased, measuring at least 5 times that of a non-porous scaffold of the same outer dimensions. In some cases, this increase can be as high as 10 or 15 times, further promoting cellular infiltration and integration.

Figure 3:
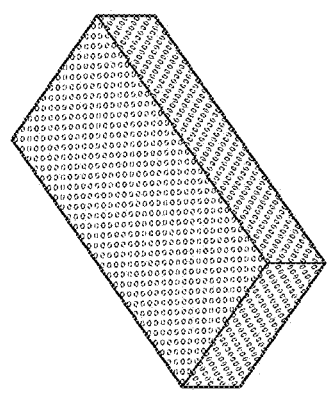
FIG. 3 illustrates the outer dimensions of a biologic matrix having a porous structure with interconnected pores emanating from its outer surfaces, as constructed in accordance with various matrix sizes.
Figure 3:
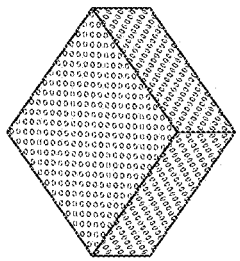
Figure 3:
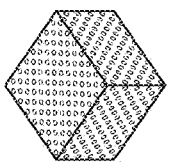
Figure 3:
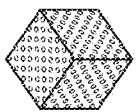

As depicted in FIG. 3, the outer dimensions of these biologic matrices can vary, coming in sizes like 2 centimeters (cm)×2 cm×2 cm, 3 cm×3 cm×2 cm, 5 cm×5 cm×2 cm, and 10 cm×5 cm×2 cm.

The porous structure of the matrix creates interstitial voids within the scaffold, facilitating cellular infiltration within two weeks post-implant, integration of native collagen within three weeks post-implant, and complete remodeling by twelve weeks post-implant. This dynamic process significantly enhances wound healing and tissue regeneration outcomes.

Moreover, the biologic matrix may incorporate antimicrobial agents, such as silver or methylene blue, which are infused into the vascular pathways of the mammalian organ or tissue following the decellularization process. This feature enhances the matrix's efficacy in preventing infection and promoting wound healing.

Additionally, the scaffold can be designed to be transparent or translucent, providing the advantage of visually monitoring the wound site without the need for removal. This transparency allows for real-time assessment of the healing progress, offering valuable insights for medical practitioners.

The biologic matrices can be engineered with sufficient mechanical strength to be suturable or stapled to the body tissue surrounding the wound site, ensuring stable and secure integration. This feature allows for the convenient application and retention of the matrix during the healing process.

Example Determination of Surface Areas of Porous Biologic Matrix Samples:

Purpose: The test aimed to determine the surface area of 10 biologic matrix samples using depth profile analysis.

Specimens: The specimens tested were in the shape of 2 cm×2 cm×2 cm cubes. Each sample was labeled as Lot 01221D REF 3000 and named Sample 1 to Sample 10.

Test Equipment: The test used the Microcontact Angle Meter model MCA-3 by Kyowa Interface Science Co., Ltd. This instrument is designed for measuring contact angles at the microscale and is commonly used for microscopic patterns, thin filaments, wires, and more. The test conditions included a camera system to capture images of the surface with high-speed options.

Test Procedure: To obtain depth profiles, two areas on one face of each cube were analyzed. The top-down camera captured images of the surface at different levels as the stage was raised in steps. The images were then analyzed using software to determine the surface area. The field of view for each image was 2.8 mm×2.1 mm.

Test Results: The surface area data for each tested specimen is shown in Table 1 below, along with the average and standard deviation. The surface area divided by the projected area (field of view) for each specimen is presented in Table 2 below. The analysis included two areas on each sample, approximately 7 mm and 14 mm from the left edge along the midpoint of the y-axis.

TABLE 1

| | Surface Area (mm$^2$) | | | |
|---|---|---|---|---|
| Sample | Area 1 | Area 2 | Average | S. D. |
| Sample 1 | 99.48 | 93.10 | 96.29 | 4.51 |
| Sample 2 | 124.90 | 152.50 | 138.70 | 19.52 |
| Sample 3 | 83.65 | 126.10 | 104.88 | 30.02 |
| Sample 4 | 93.47 | 121.60 | 107.54 | 19.89 |
| Sample 5 | 122.50 | 131.30 | 126.90 | 6.22 |
| Sample 6 | 106.20 | 120.60 | 113.40 | 10.18 |
| Sample 7 | 112.00 | 110.30 | 111.15 | 1.20 |
| Sample 8 | 116.50 | 122.30 | 119.40 | 4.10 |
| Sample 9 | 110.40 | 96.40 | 103.40 | 9.90 |
| Sample 10 | 105.80 | 100.00 | 102.90 | 4.10 |
| Total | | | 112.46 | 16.06 |

TABLE 2

| | Surface Area/Projected Area Ratio | | | |
|---|---|---|---|---|
| Sample | Area 1 | Area 2 | Average | S. D. |
| Sample 1 | 16.92 | 15.83 | 16.38 | 0.77 |
| Sample 2 | 21.24 | 25.94 | 23.59 | 3.32 |
| Sample 3 | 14.23 | 21.45 | 17.84 | 5.10 |
| Sample 4 | 15.90 | 20.68 | 18.29 | 3.38 |
| Sample 5 | 20.83 | 22.33 | 21.58 | 1.06 |
| Sample 6 | 18.06 | 20.51 | 19.29 | 1.73 |
| Sample 7 | 19.05 | 18.76 | 18.90 | 0.20 |
| Sample 8 | 19.81 | 20.80 | 20.31 | 0.70 |
| Sample 9 | 18.78 | 16.39 | 17.59 | 1.68 |
| Sample 10 | 17.99 | 17.01 | 17.50 | 0.70 |
| Total | | | 19.13 | 2.73 |

Methods of Manufacturing Biologic Matrices:

The present subject matter provides a method for manufacturing the collagen biologic matrix. This involves obtaining a mammalian organ or vascularized portion thereof or a vascularized mammalian tissue. The obtained organ or tissue is decellularized via perfusion decellularization through vascular pathways. Subsequently, the decellularized organ or tissue is suspended and inflated, including forcing a gas through the vascular pathways, causing the organ or tissue to expand three-dimensionally relative to its non-inflated configuration.

In certain embodiments, decellularizing the organ or tissue includes changing it from an opaque state to a transparent or translucent state. The decellularization process renders the tissue acellular while preserving its extracellular matrix components.

In other embodiments, forcing the gas through the vascular pathways includes creating a matrix scaffold with a resiliency ranging from 90.5% and 99.5%. In certain embodiments, the matrix scaffold has a resiliency between 93% and 98%, inclusive. The resiliency value indicates how well the scaffold retains its shape and elasticity after compression.

To calculate the resiliency, the percentage change in height after compression is determined by dividing the final height of the scaffold by its initial height and then multiplying the result by 100. In a study, fifteen matrix scaffold samples were used with starting thicknesses ranging from 1.92 cm and 2.45 cm and final thicknesses ranging from 1.91 cm and 2.39 cm. The compression was performed at a rate of 50 mm/min.

The results showed that the resiliency values ranged from 90.71% to 99.43%, with a median value of 95.84%, an average value of 95.85%, and a standard deviation of 2.33%.

Moreover, the method may include perfusing an antimicrobial agent into the vascular pathways of the organ or tissue following its decellularization. This step enhances the matrix's antimicrobial properties, contributing to infection prevention at the wound site.

The biologic matrix's porous structure, with interconnected pores emanating from the outer surface, results from the inflation process through the vascular pathways.

Figure 4:
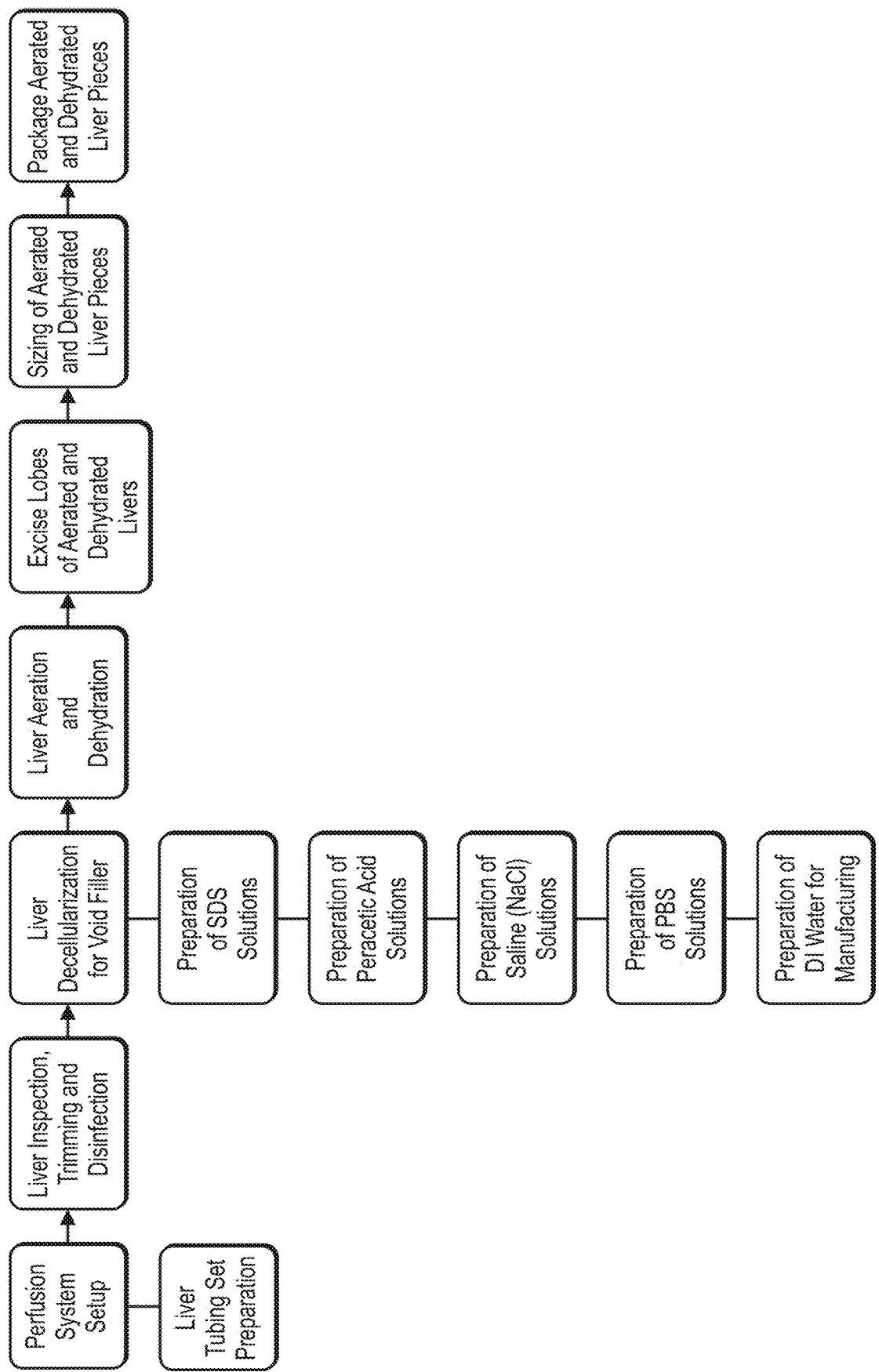
FIG. 4 illustrates a manufacturing method for a biologic matrix, as constructed in accordance with at least one embodiment.

As shown in FIG. 4, a specific manufacturing method for a biologic matrix is provided. This method involves obtaining a mammalian organ or a vascularized portion thereof or a vascularized mammalian tissue, followed by decellularization through perfusion decellularization utilizing vascular pathways. Subsequently, the decellularized organ or tissue is inflated using a gas or gas with particles or droplets (vapor) introduced into at least one vessel, duct, or cavity, causing the organ or tissue to expand three-dimensionally relative to its non-inflated configuration. The resulting scaffold can be cut to a desired size and has a density ranging from about 2 milligrams per cubic centimeter ($mg/cm^3$) to about 20 $mg/cm^3$, inclusive. For example, the density may preferably fall within the range of 3 $mg/cm^3$ to 10 $mg/cm^3$ or 4 $mg/cm^3$ to 9 $mg/cm^3$.

Moreover, the decellularization process can convert the organ or tissue from an opaque state to a transparent or translucent state, further enhancing its visual monitoring capabilities.

The matrix scaffold, with its specific resiliency value between 90.5% and 99.5%, ensures it retains its shape and elasticity after compression, offering optimal support and durability.

Additionally, an antimicrobial agent can be perfused into the vascular pathways following decellularization, enhancing the matrix's antimicrobial properties.

Furthermore, the method may include creating a matrix scaffold comprising a plurality of pores, generating an enhanced surface area as previously described.

The resulting biologic matrix, with its unique features, offers a solution for wound care and tissue engineering. The scaffold's enhanced surface area, porosity, mechanical strength, and/or antimicrobial properties collectively contribute to accelerated wound healing and improved patient outcomes. The transparent or translucent characteristics allow for non-invasive visual monitoring, facilitating precise assessment and treatment adjustments.

Figure 5:
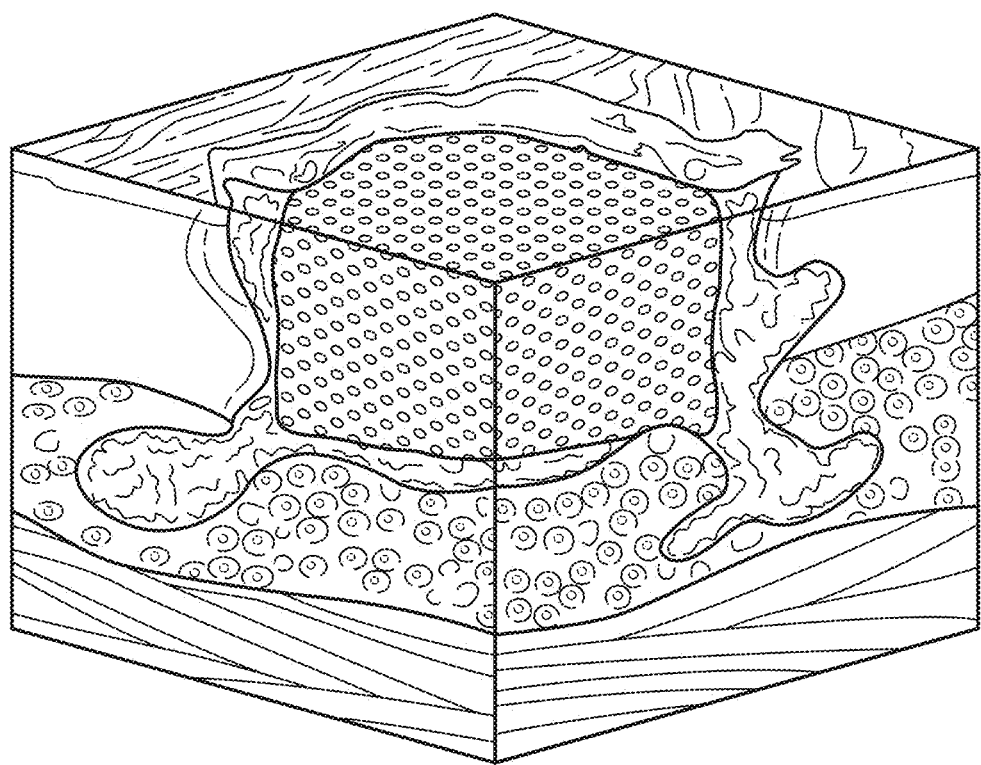
FIG. 5 illustrates a method for augmenting a void or treating a wound in a body cavity by applying a three-dimensional, biologic matrix and granular pieces thereof to the site of a void or body cavity, as arranged in accordance with at least one embodiment.
Figure 6:
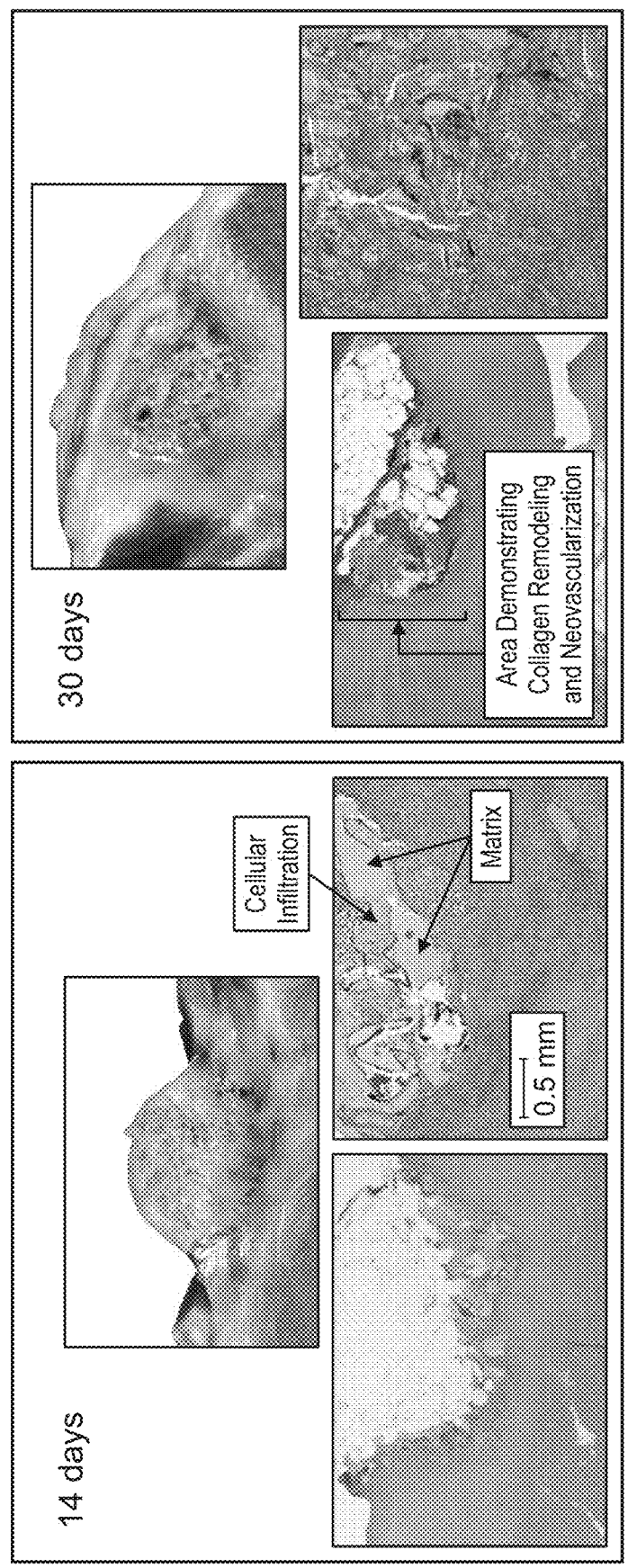
FIG. 6 illustrates cellular infiltration, integration, and remodeling of body tissue into one or more vascular pathways of a biologic matrix's scaffold.

Methods of Using Biologic Matrices for Wound Healing:

A method for treating wounds or filling voids in a mammal's body cavity can involve using a three-dimensional, resorbable collagen scaffold, along with optional granular pieces, placed directly at the affected area, as seen in FIG. 5. This scaffold comes from a vascularized part of a perfusion-decellularized mammalian organ or tissue, allowing surrounding body tissue to infiltrate, integrate, and remodel around the scaffold's vascular pathways. This method promotes effective wound healing and tissue regeneration while ensuring proper cellular infiltration and integration. In FIG. 6, the progress of a biologic matrix scaffold over time can be observed. After two weeks, cellular infiltration was visible around the edges of the three-dimensional collagen scaffold. During gross necropsy, clear signs of adhesion and integration were found between the scaffold and the nearby native porcine tissue. By the fourth week, deeper infiltration, integration, and neovascularization occurred within the scaffold. Collagen remodeling was also evident, with some areas showing nearly complete resorption of the scaffold by the fourth week.

In one embodiment, as shown in FIGS. 5 and 6, the scaffold is applied by making contact with at least three surfaces of the surrounding body tissue. This facilitates the start of cellular infiltration and tissue remodeling, leading to successful tissue regeneration and wound healing. In some cases, it may be beneficial to have contact with at least five surfaces of the scaffold with the surrounding body tissue to improve the treatment's effectiveness.

The scaffold used in the method includes a plurality of pores, providing increased surface area for cellular infiltration and tissue integration. The surface area of the scaffold, considering the plurality of pores, is at least 5 times, 10 times, or 15 times or more that of a scaffold of the same outer dimensions devoid of pores.

This porous structure promotes better tissue regeneration and wound healing processes.

Additionally, the scaffold may have a defined density within the range of 2 $mg/cm^3$ and 20 $mg/cm^3$, inclusive. This density range ensures that the scaffold possesses the required mechanical strength and structural integrity while facilitating proper tissue regeneration and remodeling.

The method involves compressing the scaffold and placing it subcutaneously into the void or body cavity. The scaffold may be configured to expand to fill the void or body cavity, ensuring complete apposition and conformity to the wound site. The scaffold is designed to maintain its shape during the wound remodeling process, facilitating the healing process.

The cellular infiltration, integration, and remodeling of surrounding body tissue into the scaffold's vascular pathways are carefully managed to promote optimal healing. Cellular infiltration is encouraged during the two-week period post-implant, integration of native collagen occurs during the three-week period post-implant, and full remodeling is expected during the twelve-week period post-implant.

In certain embodiments, the scaffold may be hydrated with saline or lactated Ringer's solution to support tissue regeneration. Moreover, to prevent infection, antimicrobial agents, such as silver nanoparticles, methylene blue, or iodine-based compounds, may be released at the site of the void or body cavity. This antimicrobial agent inhibits infection, thereby promoting a sterile environment for the wound healing process.

To protect the scaffold and wound site, a protective layer or bandage may be applied. Additionally, the scaffold can be attached to the surrounding body tissue using sutures or staples, ensuring stability and proper integration.

In specific cases where void or cavity irregularities exist, a population of milled fibers with a length of 40 millimeters or less may be placed in the undermining void or cavity irregularities before filling the main void or body cavity with the scaffold, as shown in FIG. 5. This additional step aids in achieving proper tissue regeneration and wound healing.

The methods of use can effectively treat various types of wounds, including partial or full-thickness wounds, pressure ulcers, venous ulcers, chronic vascular ulcers, diabetic ulcers, tunneling wounds, trauma wounds, draining wounds, lower limb ulcers, and surgical wounds. The use of the three-dimensional, resorbable collagen scaffold derived from a vascularized portion of a perfusion-decellularized mammalian organ or tissue ensures a natural and efficient wound healing process with reduced risk of complications.

CLOSING NOTES

This patent document discloses novel biologic matrices for wound sites, comprising three-dimensional, resorbable collagen scaffolds derived from perfusion-decellularized mammalian organs or tissues. The matrices possess a porous structure with interconnected pores, enhancing their effective surface area and promoting accelerated wound healing and improved tissue integration. The matrices can incorporate antimicrobial agents, be transparent or translucent, and possess sufficient mechanical strength for suturing or stapling. This document also encompasses methods for manufacturing and using the biologic matrices for wound healing and tissue regeneration applications.

The Detailed Description above contains references to accompanying drawings, which are part of the Detailed Description. When reading the Detailed Description, it should be referred to alongside the drawings. The purpose of these drawings is to illustrate specific embodiments in which the biologic matrices and related methods can be used. These embodiments are also called "examples" in this context.

The Detailed Description above is meant to be illustrative and not restrictive. For instance, the examples described above, or one or more features or components thereof, can be combined with each other. Additionally, various features or components can be grouped together to simplify the disclosure. However, this should not be misunderstood as indicating that an unclaimed disclosed feature is essential to any claim. The inventive subject matter can lie in less than all the features of a particular disclosed embodiment. Therefore, the following claim examples are included in the Detailed Description, with each example considered as a separate embodiment on its own.

In Example 1, a biologic matrix for a wound site comprises a three-dimensional, resorbable collagen scaffold derived from a vascularized portion of a perfusion-decellularized mammalian organ or tissue. The scaffold includes a plurality of pores emanating from one or more of its outer surfaces. The surface area of the scaffold that takes into consideration the plurality of pores is at least 5 times that of a surface area of a scaffold of the same outer dimensions that is devoid of pores.

In Example 2, the biologic matrix of Example 1 is optionally configured such that the surface area of the scaffold that takes into consideration the plurality of pores is at least 10 times that of the surface area of the scaffold of the same outer dimensions that is devoid of pores.

In Example 3, the biologic matrix of Example 1, wherein the surface area of the scaffold that takes into consideration the plurality of pores is at least 15 times that of the surface area of the scaffold of the same outer dimensions that is devoid of pores.

In Example 4, the biologic matrix of any one of Examples 1-3 is optionally configured such that a resiliency of the scaffold is between 90.5% and 99.5%, inclusive.

In Example 5, the biologic matrix of any one of Examples 1-4 is optionally configured such that the scaffold is compressible between 48% and 52% of its original thickness when a force ranging from 3 Newtons (N) and 30 N is applied to its surface. In a study, fifteen matrix scaffold samples were used with starting thicknesses ranging from 1.92 cm and 2.45 cm. Under compression, their final thicknesses were between 48% and 52% of their stating thicknesses. The compression was performed at a rate of 50 mm/min. The results showed that the force values needed to achieve a reduction in thickness of approximately half ranged from 3 N to 30 N, with a median value of 13.46 N, an average value of 14.28 N, and a standard deviation of 8.12 N.

In Example 6, the biologic matrix of any one or any combination of Examples 1-5 is optionally configured such that the plurality of pores provides a plurality of interstitial voids.

In Example 7, the biologic matrix of Example 6 is optionally configured such that the plurality of interstitial voids is sized to allow for cellular infiltration by two weeks post-implant, integration of native collagen by three weeks post-implant, and full remodeling by twelve weeks post-implant.

In Example 8, the biologic matrix of any one or any combination of Examples 1-7 can optionally be configured such that the scaffold includes an antimicrobial agent selected from silver or methylene blue, and wherein the antimicrobial agent is perfused into the vascular pathways of the mammalian organ or tissue following its perfusion decellularization.

In Example 9, the biologic matrix of any one or any combination of Examples 1-8 can optionally be configured such that the scaffold is cross-linked using chemical cross-linking agents, physical cross-linking methods, or enzymatic cross-linking to enhance its mechanical strength and stability.

In Example 10, the biologic matrix of any one or any combination of Examples 1-9 can optionally be configured such that the scaffold is transparent or translucent, enabling visual monitoring of the wound site without the need for removal.

In Example 11, the biologic matrix of any one or any combination of Examples 1-10 can optionally be configured such that the scaffold has sufficient mechanical strength to be suturable to body tissue surrounding the wound site.

In Example 12, the biologic matrix of any one or any combination of Examples 1-11 can optionally be configured such that the scaffold has sufficient mechanical strength to be stable to body tissue surrounding the wound site.

In Example 13, a biologic matrix for a wound site comprises a three-dimensional, resorbable collagen scaffold derived from a vascularized portion of a perfusion-decellularized mammalian organ or tissue. The scaffold includes a porous structure comprising a plurality of interconnecting pores emanating from one or more outer surfaces of the scaffold. The plurality of interconnecting pores is formed by intact vascular pathways of the perfusion-decellularized mammalian organ or tissue. The density of the scaffold is between 2 mg/cm$^3$ and 20 mg/cm$^3$, inclusive.

In Example 14, the biologic matrix of Example 13 is optionally configured such that the scaffold includes an antimicrobial agent selected from silver or methylene blue, and wherein the antimicrobial agent is perfused into the vascular pathways of the mammalian organ or tissue following its perfusion decellularization.

In Example 15, the biologic matrix of any one of Examples 13 or 14 can optionally be configured such that the scaffold is transparent or translucent, enabling visual monitoring of the wound site without the need for removal.

In Example 16, the biologic matrix of any one or any combination of Examples 13-15 can optionally be configured such that the scaffold has sufficient mechanical strength to be suturable to body tissue surrounding the wound site.

In Example 17, the biologic matrix of any one or any combination of Examples 13-16 can optionally be configured such that the scaffold has sufficient mechanical strength to be stable to body tissue surrounding the wound site.

In Example 18, a method for manufacturing a collagen matrix comprises obtaining a mammalian organ or a vascularized portion thereof or a vascularized mammalian tissue.

Decellularizing the organ or tissue via perfusion decellularization through vascular pathways of the organ or tissue. Inflating the decellularized organ or tissue, including forcing a gas through the vascular pathways such that the organ or tissue expands three-dimensionally relative to its non-inflated configuration and to a density of between 2 mg/cm$^3$ and 20 mg/cm$^3$, inclusive.

In Example 19, the method of Example 18 can optionally be configured such that decellularizing the organ or tissue includes changing the organ or tissue from an opaque state to a transparent or translucent state.

In Example 20, the method of any one of Examples 18 or 19 can optionally be configured such that forcing the gas through the vascular pathways includes creating a matrix scaffold that has a resiliency between 90.5% and 99.5%, inclusive.

In Example 21, the method of any one or any combination of Examples 18-20 optionally further comprises perfusing an antimicrobial agent into the vascular pathways of the organ or tissue following its decellularization.

In Example 22, the method of any one or any combination of Examples 18-21 can optionally be configured such that forcing the gas through the vascular pathways includes creating a matrix scaffold comprising a plurality of pores.

In Example 23, the method of Example 22 is optionally configured such that a surface area of the scaffold that takes into consideration the plurality of pores is at least 5 times that of a surface area of a scaffold of the same outer dimensions that is devoid of pores.

In Example 24, the method of Example 22 is optionally configured such that a surface area of the scaffold that takes into consideration the plurality of pores is at least 10 times that of a surface area of a scaffold of the same outer dimensions that is devoid of pores.

In Example 25, the method of Example 22 is optionally configured such that a surface area of the scaffold that takes into consideration the plurality of pores is at least 15 times that of a surface area of a scaffold of the same outer dimensions that is devoid of pores.

Throughout this patent document, certain terms are used to refer to features or components. It's important to note that different people may use different names for the same or similar feature or component. This patent document does not intend to distinguish between components or features that have different names but perform the same function.

For the terms defined below, specific definitions will apply, unless a different definition is given elsewhere in this patent document. The terms "a," "an," and "the" are used to include one or more than one, regardless of whether "at least one" or "one or more" is used elsewhere. The term "or" is used in a nonexclusive sense, so "A or B" includes "A but not B," "B but not A," and "A and B." "Decellularized" or "decellularization" refers to a biostructure (like an isolated organ, portion of an organ, or tissue) from which cellular and tissue content has been removed, leaving an intact acellular framework. Organs like the kidney can be composed of various specialized tissues, and the supporting fibrous network is called the stroma. The process of decellularization removes the cellular portion of the tissue, leaving a three-dimensional network of ECM made primarily of collagen, along with other proteins secreted by cells, such as cytokines, proteoglycans, laminin, and fibrillin. Decellularized biostructures can be rigid or semi-rigid, capable of altering their shapes. Examples of decellularized isolated organs include solid organs like the heart, kidney, liver, lung, pancreas, brain, bone, spleen, and bladder, as well as organs like the uterus, ureter, and urethra. All numeric values are assumed to be modified by the term "about," whether explicitly indicated. The term "about" means a number or a range of numbers that one skilled in the art considers equivalent to the stated value in terms of function or result. When a numerical range is given by endpoints, it includes all numbers and sub-ranges within and bounding that range. For example, 1 to 4 includes 1, 1.5, 1.75, 2, 2.3, 2.6, 2.9, and so on, as well as ranges like 1 to 1.5, 1 to 2, 1 to 3, 2 to 3.5, 2 to 4, 3 to 4, and so forth.

The scope of the present biologic matrices and related methods should be determined by referring to the appended claims and all equivalents that these claims are entitled to. In the appended claims, the terms "including" and "in which" are used in the same way as "comprising" and "wherein." Moreover, in the following claims, "including" and "comprising" are open-ended, meaning a device, assembly, kit, or method that includes additional features or components beyond those listed after such a term in a claim is still considered to fall within the scope of that claim. Furthermore, the terms "first," "second," "third," etc. used in the claims are merely labels and do not impose numerical requirements on the objects they refer to.

The Abstract is provided to give the reader a quick understanding of the technical disclosure. However, it should not be used to interpret or limit the scope or meaning of the claims.

What is claimed is:

1. A biologic matrix for a wound site, comprising:
a three-dimensional, resorbable, acellular collagen scaffold derived from a vascularized portion of a mammalian organ or tissue that has undergone a perfusion-decellularization process to remove cellular content,
wherein the scaffold has a uniform, interconnected pore network continuous with its preserved vascular tree, extending from internal vasculature to its outer surface,
wherein the scaffold is dried via suspended inflation to achieve a bulk density of 2 to 10 milligrams per cubic centimeter, inclusive, and
wherein the scaffold includes a plurality of pores and a surface area, which takes into consideration the plurality of pores, that is at least 10 times greater than a non-porous scaffold of the same outer dimensions.

2. The matrix of claim 1, wherein the surface area of the scaffold that takes into consideration the plurality of pores is at least 15 times greater than a non-porous scaffold of the same outer dimensions.

3. The matrix of claim 1, wherein the surface area of the scaffold that takes into consideration the plurality of pores is at least 20 times greater than a non-porous scaffold of the same outer dimensions.

4. The matrix of claim 1, wherein the scaffold has a resiliency between 90.5% and 99.5%, inclusive.

5. The matrix of claim 1, wherein the scaffold has a compressibility between 48% and 52%, inclusive, of its original thickness under a compressive force ranging from 3 Newtons and 30 Newtons, inclusive.

6. The matrix of claim 1, wherein the plurality of pores provides a plurality of interstitial voids.

7. The matrix of claim 6, wherein the plurality of interstitial voids is sized to allow for cellular infiltration by two weeks post-implant, integration of native collagen by three weeks post-implant, and full remodeling by twelve weeks post-implant.

8. The matrix of claim 1, wherein the scaffold includes an antimicrobial agent selected from silver or methylene blue, and wherein the antimicrobial agent is perfused via the preserved vascular tree after decellularization and before drying.

9. The matrix of claim 1, wherein the scaffold is cross-linked using chemical cross-linking agents, physical cross-linking methods, or enzymatic cross-linking to enhance its mechanical strength and stability.

10. The matrix of claim 1, where the scaffold is transparent or translucent after drying, allowing visual inspection of underlying tissue through the scaffold.

11. The matrix of claim 1, wherein the scaffold is suturable to body tissue surrounding the wound site.

12. The matrix of claim 1, wherein the scaffold is staplable to body tissue surrounding the wound site.

13. A biologic matrix for a wound site, comprising:

a three-dimensional, resorbable, acellular collagen scaffold derived from a vascularized portion of a perfusion-decellularized, suspension-dried mammalian organ or tissue, wherein the scaffold comprises a uniform, interconnected pore network continuous with its preserved vascular tree, extending from internal vasculature to its outer surface, wherein the scaffold includes a plurality of pores and a surface area, which takes into consideration the plurality of pores, that is at least 20 times greater than a non-porous scaffold of the same outer dimensions, and wherein the scaffold has a bulk density between 3 and 10 milligrams per cubic centimeter, inclusive.

14. The matrix of claim 13, wherein the scaffold includes an antimicrobial agent selected from silver or methylene blue, and wherein the antimicrobial agent is perfused via the preserved vascular tree after decellularization and before drying.

15. The matrix of claim 13, where the scaffold is transparent or translucent after drying, allowing visual inspection of underlying tissue through the scaffold.

16. The matrix of claim 13, wherein the scaffold is suturable to body tissue surrounding the wound site.

17. The matrix of claim 13, wherein the scaffold is staplable to body tissue surrounding the wound site.

* * * * *